US00PP18994P2

(12) United States Plant Patent
Smith

(10) Patent No.: US PP18,994 P2
(45) Date of Patent: Jul. 1, 2008

(54) *CHRYSANTHEMUM* PLANT NAMED 'YOTHERESA'

(50) Latin Name: *Chrysanthemum×morifolium*
Varietal Denomination: Yotheresa

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 11/641,402

(22) Filed: Dec. 18, 2006

(51) Int. Cl.
*A01H 5/00* (2006.01)

(52) U.S. Cl. ..... Plt./292

(58) Field of Classification Search ..... Plt./292
See application file for complete search history.

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of *Chrysanthemum* plant named 'Yothersea', characterized by its compact, upright and outwardly spreading plant habit; freely branching habit; dense and full plant habit; uniform and freely flowering habit; daisy-type inflorescences with elongated oblong to ligulate-shaped ray florets; purple-colored ray florets; and natural season flowering about September 21$^{st}$ in the Northern Hemisphere.

1 Drawing Sheet

Botanical designation: *Chrysanthemum×morifolium.*
Cultivar denomination: 'YOTHERESA'.

BACKGROUND OF THE INVENTION

The present invention relates to a new and distinct cultivar of *Chrysanthemum* plant, botanically known as *Chrysanthemum×morifolium,* commercially grown as a garden *Chrysanthemum* and hereinafter referred to by the name 'Yotheresa'.

The objective of the breeding program is to create new garden-type *Chrysanthemum* cultivars having inflorescences with desirable inflorescence forms, attractive floret colors and good garden performance.

The new *Chrysanthemum* originated from a cross-pollination made by the Inventor in February, 2003, in Salinas, Calif. of the *Chrysanthemum×morifolium* cultivar Gedi Two Cop, disclosed in U.S. Plant Pat. No. 14,404, as the female, or seed, parent with the *Chrysanthemum×morifolium* cultivar Yonatasha, disclosed in U.S. Plant Pat. No. 13,907, as the male, or pollen, parent. The new *Chrysanthemum* was discovered and selected by the Inventor as a single flowering plant within the progeny of the stated cross-pollination in a controlled environment in Alva, Fla. in September, 2003.

Asexual reproduction of the new *Chrysanthemum* by vegetative cuttings was first conducted in Alva, Fla. in December, 2003. Asexual reproduction by cuttings has shown that the unique features of this new *Chrysanthemum* are stable and reproduced true to type in successive generations.

SUMMARY OF THE INVENTION

Plants of the cultivar Yotheresa have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yotheresa'. These characteristics in combination distinguish 'Yotheresa' as a new and distinct garden *Chrysanthemum* cultivar.

1. Compact, upright and outwardly spreading plant habit.
2. Freely branching habit; dense and full plant habit.
3. Uniform and freely flowering habit.
4. Daisy-type inflorescences with elongated oblong to ligulate-shaped ray florets.
5. Purple-colored ray florets.
6. Natural season flowering about September 21$^{st}$ in the Northern Hemisphere.

In side-by-side comparisons conducted in Alva, Fla., plants of the new *Chrysanthemum* differed from plants of the female parent, the cultivar Gedi Two Cop, in the following characteristics:

1. Plants of the new *Chrysanthemum* were smaller than plants of the cultivar Gedi Two Cop.
2. Plants of the new *Chrysanthemum* flowered about one month earlier than plants of the cultivar Gedi Two Cop when grown under natural season conditions.
3. Plants of the new *Chrysanthemum* had larger inflorescences than plants of the cultivar Gedi Two Cop.
4. Plants of the new *Chrysanthemum* and the cultivar Gedi Two Cop differed in inflorescence form.
5. Ray florets of plants of the new *Chrysanthemum* were darker in color than ray florets of plants of the cultivar Gedi Two Cop.

In side-by-side comparisons conducted in Alva, Fla., plants of the new *Chrysanthemum* differed from plants of the male parent, the cultivar Yonatasha, in the following characteristics:

1. Plants of the new *Chrysanthemum* and the cultivar Yonatasha differed in ray floret color as plants of the cultivar Yonatasha had light purple-colored ray florets.
2. Ray floret color of plants of the new *Chrysanthemum* faded slower than ray floret color of plants of the cultivar Yonatasha.

Plants of the new *Chrysanthemum* can be compared to plants of the *Chrysanthemum* cultivar Yocecilia, disclosed in U.S. Plant Pat. No. 13,798. In side-by-side comparisons conducted in Alva, Fla., plants of the new *Chrysanthemum* differed from plants of the cultivar Yocecilia in the following characteristics:

1. Plants of the new *Chrysanthemum* were smaller than plants of the cultivar Yocecilia.
2. Plants of the new *Chrysanthemum* had larger inflorescences than plants of the cultivar Yocecilia.
3. Plants of the new *Chrysanthemum* and the cultivar Yocecilia differed in ray floret color as plants of the cultivar Yocecilia had light purple-colored ray florets.
4. Ray floret color of plants of the new *Chrysanthemum* faded slower than ray floret color of plants of the cultivar Yocecilia.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the bottom of the sheet comprises a side perspective view of a typical flowering plant of 'Yotheresa'.

The photograph at the top of the sheet is a close-up view of typical inflorescences of 'Yotheresa'.

DETAILED BOTANICAL DESCRIPTION

The aforementioned photographs and following observations and measurements describe plants grown in Fletcher, N.C. during the summer in an outdoor nursery and under conditions and practices which approximate those generally used in commercial garden *Chrysanthemum* production. During the production of the plants, day temperatures averaged 29° C. and night temperatures averaged 16° C. Plants were grown in 15-containers, exposed to long day/short night conditions and pinched about two weeks later. About two weeks after the pinch, the photoinductive short day/long night treatments were started. Plants used in the photographs and for the description were about three months old. In the following description, color references are made to The Royal Horticultural Society Colour Chart, 1995 Edition, except where general terms of ordinary dictionary significance are used.

Botanical classification: *Chrysanthemum×morifolium* cultivar Yotheresa.

Parentage:

*Female, or seed, parent.*—*Chrysanthemum×morifolium* cultivar Gedi Two Cop, disclosed in U.S. Plant Pat. No. 14,404.

*Male, or pollen, parent.*—*Chrysanthemum×morifolium* cultivar Yonatasha, disclosed in U.S. Plant Pat. No. 13,907.

Propagation:

*Type.*—Terminal vegetative cuttings.

*Time to initiate roots.*—About four days at temperatures of about 21° C.

*Time to produce a rooted young plant.*—About ten to twelve days at temperatures of about 21° C.

*Root description.*—Fine, fibrous; white in color.

*Rooting habit.*—Freely branching.

Plant description:

*Appearance.*—Herbaceous daisy-type garden *Chrysanthemum*. Stems upright and outwardly spreading giving a uniformly mounded appearance to the plant. Freely branching habit, about seven to eight lateral branches develop after removal of terminal apex (pinching) each with numerous secondary laterals; dense and full plant habit. Strong and vigorous growth habit.

*Plant height.*—About 19 cm.

*Plant width.*—About 32 cm.

*Lateral branches.*—Length: About 17.5 cm. Diameter: About 5 mm. Internode length: About 1.3 cm. Strength: Strong. Texture: Pubescent. Color, developing: 147C. Color, older: 199B.

*Leaves.*—Arrangement: Alternate, simple. Length: about 4.2 cm. Width: About 3.1 cm. Apex: Acute. Base: Attenuate. Margin: Palmately lobed, sinuses between lateral lobes parallel to divergent. Texture, upper and lower surfaces: Fine pubescence; veins prominent on lower surface. Color: Developing foliage, upper and lower surfaces: 147A. Fully expanded foliage, upper surface: 147A; venation, close to 147B. Fully expanded foliage, lower surface: Slightly more grey than 147A; venation, close to 147B. Petiole: Length: About 1.5 cm. Diameter: About 2 mm. Texture, upper and lower surfaces: Pubescent. Color, upper surface: 137B. Color, lower surface: 137C.

Inflorescence description:

*Appearance.*—Daisy-type inflorescence form with elongated oblong to ligulate-shaped ray florets. Inflorescences borne on terminals above foliage. Disk and ray florets arranged acropetally on a capitulum. Inflorescences faintly fragrant.

*Flowering response.*—Under natural season conditions, plants flower about September 21$^{st}$ in the Northern Hemisphere. At other times of the year, inflorescence initiation and development can be induced under short day/long night conditions (at least 13.5 hours of darkness). Early flowering habit; plants exposed to photoinductive short day/long night conditions flower about 50 days later.

*Postproduction longevity.*—Inflorescences maintain good color and substance for about three weeks in an outdoor nursery.

*Quantity of inflorescences.*—About 40 inflorescences develop per lateral branch.

*Inflorescence bud.*—Height: About 1.3 cm. Diameter: about 8 mm. Shape: Oblate. Color: 77B.

*Inflorescence size.*—Diameter: About 4.8 cm. Depth (height): About 1 cm. Disc diameter: About 1.2 cm. Receptacle diameter: About 1.5 cm. Receptacle height: About 4 mm.

*Ray florets.*—Shape: Elongated-oblong to ligulate. Orientation: Initially upright, then about 90° from vertical or perpendicular to peduncle. Aspect: Initially incurved, then mostly flat. Length: About 2.5 cm. Width: About 6 mm. Apex: Emarginate. Base: Attenuate. Margin: Entire. Texture, upper and lower surfaces: Smooth, glabrous, satiny. Number of ray florets per inflorescence: About 30 arranged in two or three whorls. Color: When opening, upper surface: 77B to 77C. When opening, lower surface: 77C; narrow striations, 77B. Fully opened, upper surface: 71A. Fully opened, lower surface: 78C.

Disc florets. —Shape: Tubular, elongated. Length: About 6 mm. Diameter: About 1.5 mm. Number of disc florets per inflorescence: About 110. Color, immature: Apex: Close to 145A. Mid-section: Close to 2A. Base: Close to 157A. Color, mature: Apex: Close to 4A. Mid-section: Close to 4B. Base: Close to 157D.

*Phyllaries.*—Number of phyllaries per inflorescence: About 20 arranged in about two whorls. Length: About 7.5 mm. Width: About 2.5 mm. Shape: Elliptical. Apex: Acute. Base: Truncate. Texture, upper surface: Smooth, waxy. Texture, lower surface: Pubescent. Color, upper surface: Close to 138A; towards the margins, 157D. Color, lower surface: Close to 148B.

*Peduncles.*—Length: About 3 cm. Diameter: About 1 mm. Angle: About 45° from vertical. Strength: Strong. Texture: Pubescent; longitudinally ridged. Color: Close to 148B.

*Reproductive organs.*—Androecium: Stamen number: About five per floret. Filament length: About 2 mm. Filament color: close to 145D. Anther length: About 2 mm. Anther shape: Oblong. Anther color: Close to 4A. Pollen amount: Scarce. Pollen color: 1A. Gynoecium: Pistil length: About 6 mm. Stigma shape: Bi-parted. Stigma color: Close to 3B. Style length: About 3 mm. Style color: Close to 1C. Ovary color: Close to 157A.

*Seed/fruit.*—Seed and fruit production has not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and to tolerate temperatures from about 0° C. to about 38° C.

It is claimed:

1. A new and distinct *Chrysanthemum* plant named 'Yotheresa' as illustrated and described.

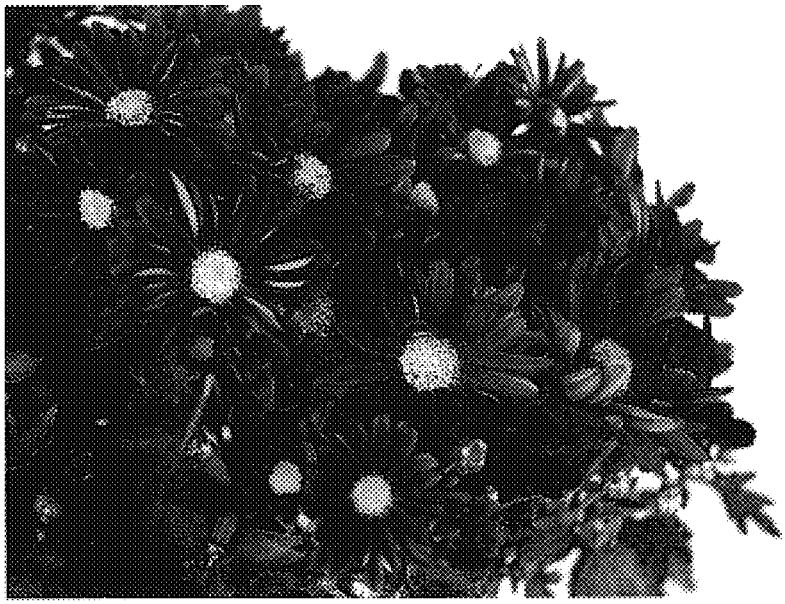
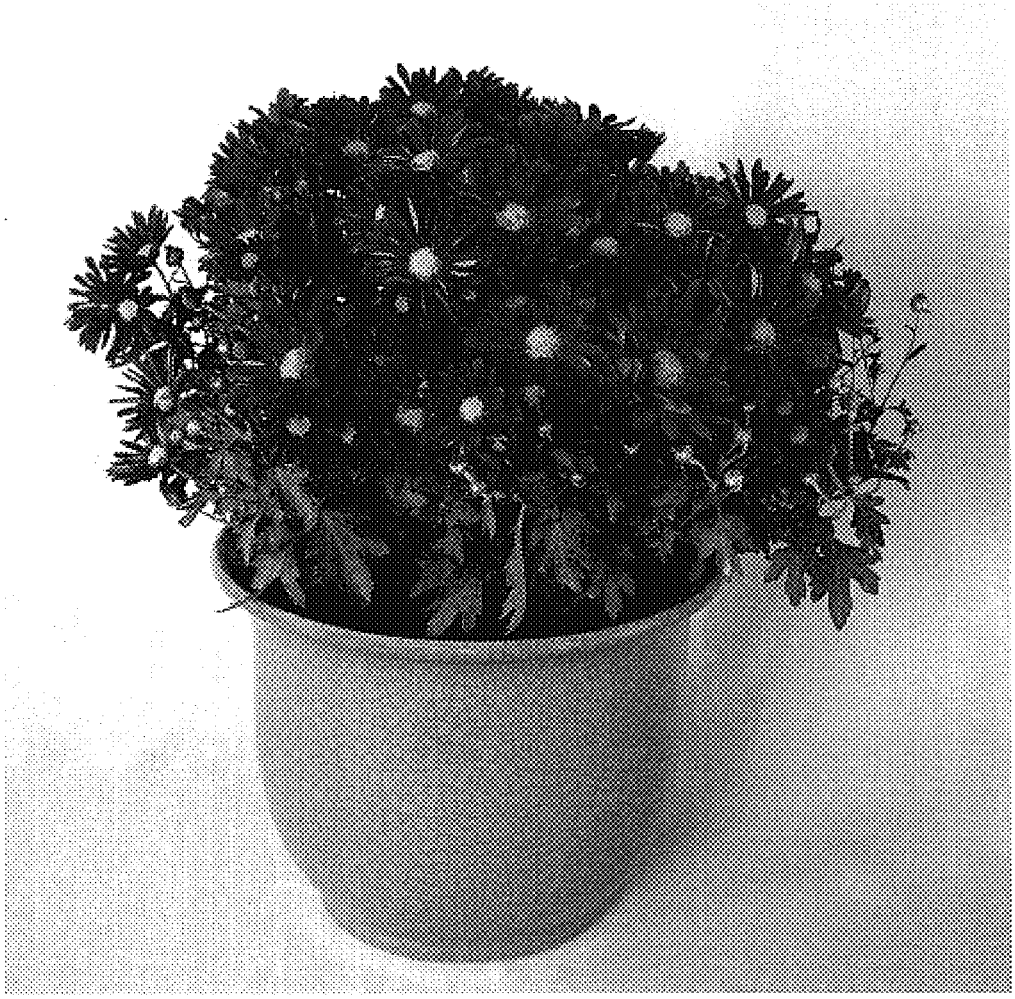

* * * * *